(12) United States Patent
Isaacs et al.

(10) Patent No.: US 7,767,648 B2
(45) Date of Patent: Aug. 3, 2010

(54) TISSUE SPECIFIC PRODRUGS

(75) Inventors: John Tod Isaacs, Phoenix, MD (US); Samuel R. Denmeade, Ellicott City, MD (US)

(73) Assignee: Genspera, Inc., San Antonio, TX (US)

( * ) Notice: Subject to any disclaimer, the term of this patent is extended or adjusted under 35 U.S.C. 154(b) by 51 days.

(21) Appl. No.: 12/323,380

(22) Filed: Nov. 25, 2008

(65) Prior Publication Data

US 2009/0163426 A1   Jun. 25, 2009

Related U.S. Application Data

(62) Division of application No. 10/432,849, filed as application No. PCT/US01/45100 on Nov. 30, 2001, now Pat. No. 7,468,354.

(60) Provisional application No. 60/250,543, filed on Dec. 1, 2000.

(51) Int. Cl.
*A61K 38/07* (2006.01)
(52) U.S. Cl. ...................................... 514/18
(58) Field of Classification Search ........................ None
See application file for complete search history.

(56) References Cited

OTHER PUBLICATIONS

Haffner, Michael C. et al., "Prostate-specific membrane antigen expression in the neovasculature of gastric and colorectal cancers," *Human Pathology*, Dec. 2009, 40(12):1754-61.
Liu, He et al., "Monoclonal Antibodies to the Extracellular Domain of Prostate-Specific Membrane Antigen Also React with Tumor Vascular Endothelium," Sep. 1, 1997, *Cancer Research* 57, 3629-3634.
Chang, Sam S. et al., "Prostate-specific Membrane Antigen is Produced in Tumor-Associated Neovasculature," *Clin. Cancer Res.*, Oct. 1999, 5:2674-2681.
Chang, Sam S. et al., "Five Different Anti-Prostate-Specific Membrane Antigen (PSMA) Antibodies Confirm PSMA Expression in Tumor-associated Neovasculature," *Cancer Res.*, Jul. 1, 1999, 59:3192-3198.
Dionne, Craig A., "G202 Pharmacology Summary", Jul. 2008, 17 pages, published in Los Angeles, California.

*Primary Examiner*—Christina Bradley
(74) *Attorney, Agent, or Firm*—Winstead PC

(57) ABSTRACT

The invention provides novel peptide prodrugs which contain cleavage sites specifically cleaved by prostate specific membrane antigen (PSMA). These prodrugs are useful for substantially inhibiting the non-specific toxicity of a variety of therapeutic drugs. PSMA is secreted by prostatic glandular cells. Upon cleavage of the prodrug by PSMA, the therapeutic drugs are activated and exert their toxicity. Sesquiterpene-γ-lactones form part of the prodrugs, and are designed to be linked to carrier moieties such as the peptides of the invention. Methods for treating cell proliferative disorders are also featured in the invention.

11 Claims, 6 Drawing Sheets

Scheme X. a) MeOH, SOCl$_2$; b) Boc-L-leucine, Boc-D-leucine or Boc-L-alanine, DIPEA, DCC, DCM; c) aq. NaOH, MeOH; d) DBTG, DCC, DMAP, DCM; e) TFA, DCM; 12a: L-6AHT, n=5, R=CH$_2$(CH$_3$)$_2$, *(S); 12b: L-12ADT, n=11, R=CH$_2$(CH$_3$)$_2$, *(S); 12c: LD-12ADT, n=11, R=CH$_2$(CH$_3$)$_2$, *(R); 12d: A-12ADT, n=11, R=CH$_3$, *(S).

Scheme X. a) MeOH, SOCl$_2$; b) Nα-Boc-L-glutamic acid γ-tert-butyl ester, DIPEA, DCC DCM; c) aq. NaOH, MeOH; d) DBTG, DCC, DMAP, DCM; e) TFA, DCM; 16: EG-12ADT, *(S).

TISSUE SPECIFIC PRODRUGS

This application is a divisional of U.S. Pat. application Ser. No. 10/432,849, filed Nov. 30, 2001, which claims priority from Provisional Application No. 60/250,543, filed Dec. 1, 2000, the entire disclosures of which are hereby incorporated by reference in their entirety for all purposes.

TECHNICAL FIELD

This invention relates generally to the targeted activation and delivery of therapeutic drugs to cells that produce prostate specific membrane antigen (PSMA) and relates more specifically to PSMA-specific peptide prodrugs that become activated to yield therapeutic drugs.

BACKGROUND

There is currently no effective therapy for men with metastatic prostate cancer who relapse after androgen ablation, even though numerous agents have been tested over the past thirty years. Prolonged administration of effective concentrations of standard chemotherapeutic agents is usually not possible because of dose-limiting systemic toxicities.

PSMA is a 100 kDa prostate epithelial cell type II transmembrane glycoprotein that was originally isolated from a cDNA library from the androgen responsive LNCaP human prostate cancer cell line, as disclosed, for example by Horoszewicz et al., *Cancer Res.* 43:1809-1818, (1980). Immunohistochemical studies using monoclonal antibodies have demonstrated that PSMA is expressed by normal prostate epithelium and is even more highly expressed by a large proportion of prostate cancers, including metastatic prostate cancers, as disclosed, for example in Horoszewicz et al.; Wright et al., *Urol. Oncol.* 1:18-28, (1995); and Lopes et al., *Cancer Res.* 50:6423-6429, (1990). Low-level detection of the PSMA protein has also been seen in the duodenal mucosa and in a subset of proximal renal tubules. In all other human tissues, including normal vascular endothelium, PSMA expression was not detectable, as disclosed for example, in Silver et al., *Clin. Cancer Res.* 3:81-85, (1997); and Chang et al., *Cancer Res.* 59:3192-3198, (1999). PSMA, however, has been detected in the neovasculature of a large number of different tumor types including breast, renal, colon, pancreatic, brain, melanoma, lung, testicular, sarcoma and transitional cell carcinomas (Silver et al., and Chang et al.).

Two discrete enzymatic functions for PSMA have been described. Carter et al., *Proc. Natl. Acad. Sci., USA* 93:749-753, (1996), demonstrated that PSMA possesses the hydrolytic properties of an N-acetylated α-linked acidic dipeptidase (NAALADase). NAALADase is a membrane hydrolase activity that is able to hydrolyze the neuropeptide N-acetyl-l-aspartyl-l-glutamate (NAAG) to yield the neurotransmitter glutamate and N-acetyl-aspartate. In addition to the NAALADase activity, PSMA also functions as a pteroyl poly-γ-glutamyl carboxypeptidase (folate hydrolase), as disclosed, for example, by Pinto et al., *Clin. Cancer Res.* 2:1445-1451, (1996). PSMA exhibits exopeptidase activity and has more recently been classified as glutamate carboxypeptidase II. It is able to progressively hydrolyze γ-glutamyl linkages of both poly-γ-glutamated folates and methotrexate analogs with varying length glutamate chains, as disclosed, for example, in Pinto et al., and Heston et al., *Urology* 49 (Suppl 3A): 104-112, (1997). PSMA is able to progressively hydrolyze γ-glutamyl linkages of both poly-gamma glutamated folates and poly-gamma glutamated methotrexate analogs with varying length glutamate chains. Unfortunately, it has also been found that these polyglutamated analogs can also be readily hydrolyzed by gamma glutamyl hydrolase (GGH), a lysosomal enzyme. Gingras et al. recently characterized a human blood plasma glutamate carboxypeptidase (PGCP) that has significant sequence homology to PSMA and glutamate carboxypeptidase activity, see *J. Biol. Chem.* 274:11742-11750, (1999). Proteins that are homologous to PSMA have been recently isolated from the rat brain and pig jejunum, as disclosed, for example, in Luthi-Carter et al., *Proc. Natl. Acad. Sci. USA* 95:3215-3220, (1998); and Halsted et al., *J. Biol. Chem.* 273:20417-20424, (1998). These proteins have >80% amino acid sequence homology with PSMA and possess similar enzymatic functions.

SUMMARY

The present invention provides therapeutic prodrug compositions, comprising therapeutic drugs linked to peptides, which are efficiently and specifically cleaved by PSMA. The peptides include amino acid sequences containing cleavage sites for prostate specific membrane antigen (PSMA) and other enzymes with the same overall activity and overall proteolytic specificity as PSMA. Representative amino acid sequences are provided, and include α-linked dicarboxylic amino acid-containing peptides, side chain-linked (for example, γ-linked) dicarboxylic amino acid-containing peptides, and α-, side chain-linked dicarboxylic amino acid-containing peptides, as well as analogs, derivatives and conservative variations thereof. The linkage of therapeutic drug to peptide substantially inhibits the non-specific toxicity of the drug. Cleavage of the peptide releases the drug, activating it or restoring its non-specific toxicity.

Examples of therapeutic drugs include analogs of therapeutic sesquiterpene-lactones, including derivatives of the thapsigargins. The thapsigargins are a group of natural products isolated from species of the umbelliferous genus *Thapsia*. The term thapsigargins has been defined by Christensen, et al., *Prog. Chem. Nat. Prod.*, 71 (1997) 130-165. These derivatives contain a means of linking the therapeutic drug to carrier moieties, including peptides and antibodies, including those peptides and antibodies which can specifically interact with antigens, including PSMA. The interactions can involve cleavage of the peptide to release therapeutic drugs, for example, sesquiterpene-γ-lactones, such as thapsigargin derivatives.

The invention also provides a method for treating cell proliferative disorders, including those which involve the production of PSMA, in subjects having or at risk of having such disorders. The method involves administering to the subject a therapeutically effective amount of the composition of the invention.

The invention also provides a method of producing the prodrug composition of the invention. In another embodiment, the invention provides a method of detecting PSMA activity in tissue. In yet another embodiment, the invention provides a method of selecting appropriate prodrugs for use in treating cell proliferative disorders involving PSMA-production.

The invention also provides a method for detecting a cell proliferative disorder associated with PSMA production in a tissue of a subject, comprising contacting a target cellular component suspected of having a PSMA-associated disorder, with a reagent which detects enzymatically active PSMA.

The invention also provides a method of determining PSMA activity in a PSMA-containing sample, comprising contacting the sample with a detectably labeled peptide which is specifically cleaved by PSMA for a period of time sufficient to allow PSMA to cleave the peptide, detecting the detectable label to yield a detection level, which is then compared to the detection level obtained by contacting the same detectably labeled peptide with a standard PSMA sample of known activity.

The invention also provides a method of imaging soft tissue and/or bone metastases which produce PSMA, comprising administering a lipophilic imaging label linked to a peptide which is specifically cleaved by PSMA to a subject having or suspected of having a PSMA-associated cell proliferative disorder, allowing PSMA to cleave the peptide, allowing the lipophilic imaging label to accumulate in the tissue and/or bone, allowing the subject to clear the uncleaved peptide, and imaging the subject for diagnostic purposes.

As used herein, the term "prostate specific membrane antigen" (PSMA) means prostate specific membrane antigen, as well as all other proteases that have the same or substantially the same proteolytic cleavage specificity as prostate specific membrane antigen. As used herein, "sufficiently toxic" refers to therapeutic drugs which display nonspecific toxicity toward cells with an $LC_{50}$ concentration (that is, the concentration required to kill 50% of treated cells) that is at least 3 times lower than the $LC_{50}$ concentration of the prodrugs of the invention, more preferably at least 20 times lower, and therapeutic drugs most preferably have an $LC_{50}$ concentration that is at least 100 times lower than the $LC_{50}$ concentration of the prodrugs of the invention. The term "contacting" refers to exposing tissue to the peptides, therapeutic drugs or prodrugs of the invention so that they can effectively inhibit cellular processes, or kill cells. Contacting may be in vitro, for example by adding the peptide, drug, or prodrug to a tissue culture to test for susceptibility of the tissue to the peptide, drug or prodrug. Contacting may be in vivo, for example administering the peptide, drug or prodrug to a subject with a cell proliferative disorder, such as prostate or breast cancer. By "polypeptide" is meant any chain of amino acids, regardless of length or post-translational modification (e.g., glycosylation or phosphorylation). Amino acids include the 20 common amino acids that make up human proteins as well as other unnatural amino acids that may be substituted for the common amino acids. The term amino acids also encompasses the l- and d-stereoisomers of each amino acid. As written herein, amino acid sequences are presented according to the standard convention, namely that the amino terminus of the peptide is on the left, and the carboxy terminus on the right.

Unless otherwise defined, all technical and scientific terms used herein have the ordinary meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other reference materials mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
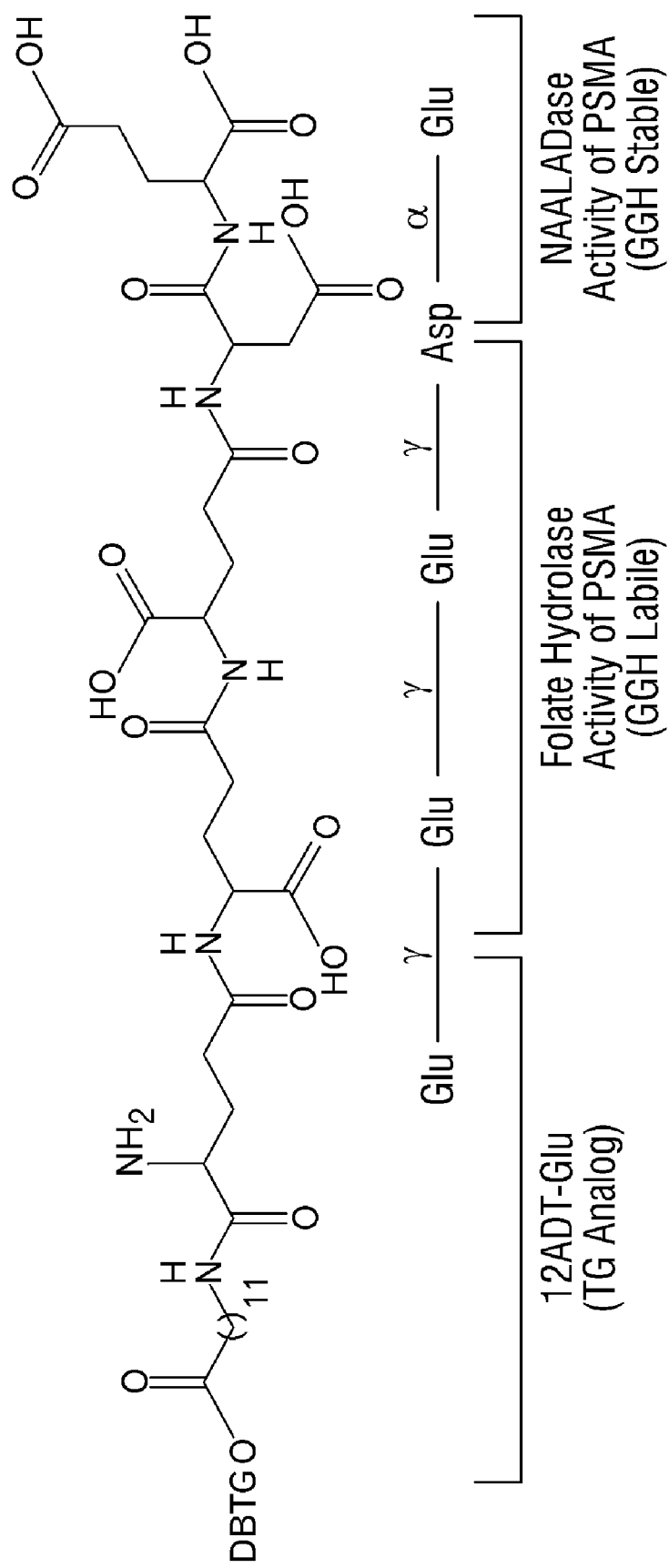
FIG. 1 is a structure of an embodiment of a PSMA-activated TG prodrug.

PSMA is expressed in high levels by prostate, and other, cancer cells but not by normal cells. The specific targeting of the killing ability of therapeutic drugs to prostate, and other, cancer cells is enabled. Therapeutic drugs, for example, thapsigargins modified in the 8-position, are directly or indirectly coupled to the α-amino, or side-chain carboxyl of a peptide including dicarboxylic acid-containing amino acids or amidated analogs thereof, for example, glutamic acid, aspartic acid, glutamine or asparagine. Linking groups can be bonded between the drugs and the peptides.

The invention involves peptides that contain a cleavage site specific for prostate specific membrane antigen (PSMA). These peptides are efficiently and specifically cleaved by PSMA. These peptides are useful for substantially inhibiting the non-specific toxicity of the therapeutic agents prior to the agents coming in proximity to tissue containing PSMA. The prodrugs of the invention comprise peptides containing a cleavage site specific for PSMA, and therapeutic drugs. The presence of the peptides substantially converts the therapeutic drug into an inactive prodrug. The prodrugs do not show significant non-specific toxicity, but in environments where PSMA is found, the prodrugs become activated upon peptide cleavage, releasing the therapeutic drug, which then exhibits its inherent non-specific toxicity.

PSMA-Specific Peptide

In one aspect, the invention features prodrugs including a peptide containing an amino acid sequence that includes a cleavage site specific for PSMA or an enzyme having a proteolytic activity of PSMA. Prodrugs are designed that can be activated by the pteroyl poly-γ-glutamyl carboxypeptidase (folate hydrolase) activity of PSMA. Gamma glutamyl hydrolase (GGH) is secreted by hepatocytes and by a variety of tumor cell types and GGH activity is present in human serum. Therefore, effective side chain-linked substrates are desirably specifically hydrolyzed by PSMA with minimal hydrolysis by GGH.

The PSMA cleavage site includes at least the dipeptide, $X_1X_2$. This peptide contains the amino acids Glu or Asp at position $X_1$. $X_2$ can be Glu, Asp, Gln, or Asn. Tripeptides $X_1X_2X_3$ are also suitable, with $X_1$ and $X_2$ defined as before, with $X_3$ as Glu, Asp, Gln or Asn. Tetrapeptides $X_1X_2X_3X_4$ are also suitable, with $X_{1-3}$ defined as above, and with $X_4$ as Glu, Asp, Gln or Asn. Pentapeptides $X_1X_2X_3X_4X_5$ are also suitable, with $X_{1-4}$ defined as above, and with $X_5$ as Glu, Asp, Gln or Asn. Hexapeptides $X_1X_2X_3X_4X_5X_6$ are also suitable, with $X_{1-5}$ defined as above, and with $X_6$ as Glu, Asp, Gln or Asn. Further peptides of longer sequence length can be constructed in similar fashion.

Generally, the peptides are of the following sequence: $X_1 \ldots X_n$, where n is 2 to 30, preferably 2 to 20, more preferably 2 to 15, and even more preferably 2 to 6, where $X_1$ is Glu, Asp, Gln or Asn, but is preferably Glu or Asp, and $X_2\text{-}X_n$ are independently selected from Glu, Asp, Gln and Asn. Some preferred peptide sequences are as above, except that $X_2\text{-}X_{n-1}$ are independently selected from Glu, and Asp, and $X_n$ is independently selected from Glu, Asp, Gln and Asn. The length of the peptide can be optimized to allow for efficient PSMA hydrolysis, enhanced solubility of therapeutic drug in aqueous solution, if this is needed, and limited non-specific cytotoxicity in vitro.

Among the α-linked dipeptides, Asp-Glu, Asp-Asp, Asp-Asn and Asp-Gln are preferably employed for use in the prodrugs described herein. Among the all α-linked tripeptides, Glu-Glu-Glu, Glu-Asp-Glu, Asp-Glu-Glu, Glu-Glu-Asp, Glu-Asp-Asp, Asp-Glu-Asp, Asp-Asp-Glu, Asp-Asp-Asp, Glu-Glu-Gln, Glu-Asp-Gln, Asp-Glu-Gln, Glu-Glu-Asn, Glu-Asp-Asn, Asp-Glu-Asn, Asp-Asp-Gln, and Asp-Asp-Asn are preferably employed for use in the prodrugs described herein. Tripeptides containing Gln or Asn in positions $X_2$ can also be desirably employed. Longer all α-linked peptides may also be employed for use in the prodrugs described herein, and such peptides with Gln or Asn in any positions $X_2\text{-}X_n$ can also be desirably employed.

Side-Chain Linkages

PSMA is also able to hydrolyze a variety of side chain-linked peptides. Particular side chain-linked, for example, γ-linked peptides are not specific for PSMA, but can also hydrolyzed by GGH. Some preferred peptides take advantage of the dual ability of PSMA to hydrolyze certain α- and side-chain linkages between aspartyl, and glutamyl residues.

Among the side chain-linked dipeptides, Glu*Asp, Glu*Asn, Glu*Glu, Glu*Gln, Asp*Asp, Asp*Glu, Asp*Asn, and Asp*Gln can be employed for use in the prodrugs described herein. Among the all side chain-linked tripeptides, Glu*Glu*Glu, Glu*Asp*Glu, Asp*Glu*Glu, Glu*Glu*Asp, Glu*Asp*Asp, Asp*Glu*Asp, Asp*Asp*Glu, Asp*Asp*Asp, Glu*Glu*Gln, Glu*Asp*Gln, Asp*Glu*Gln, Glu*Glu*Asn, Glu*Asp*Asn, Asp*Glu*Asn, Asp*Asp*Gln, and Asp*Asp*Asn can be preferably employed for use in the prodrugs described herein. Longer peptides which of analogous sequences can also be employed for use in the prodrugs described herein.

Mixed Peptides

Figure 2:
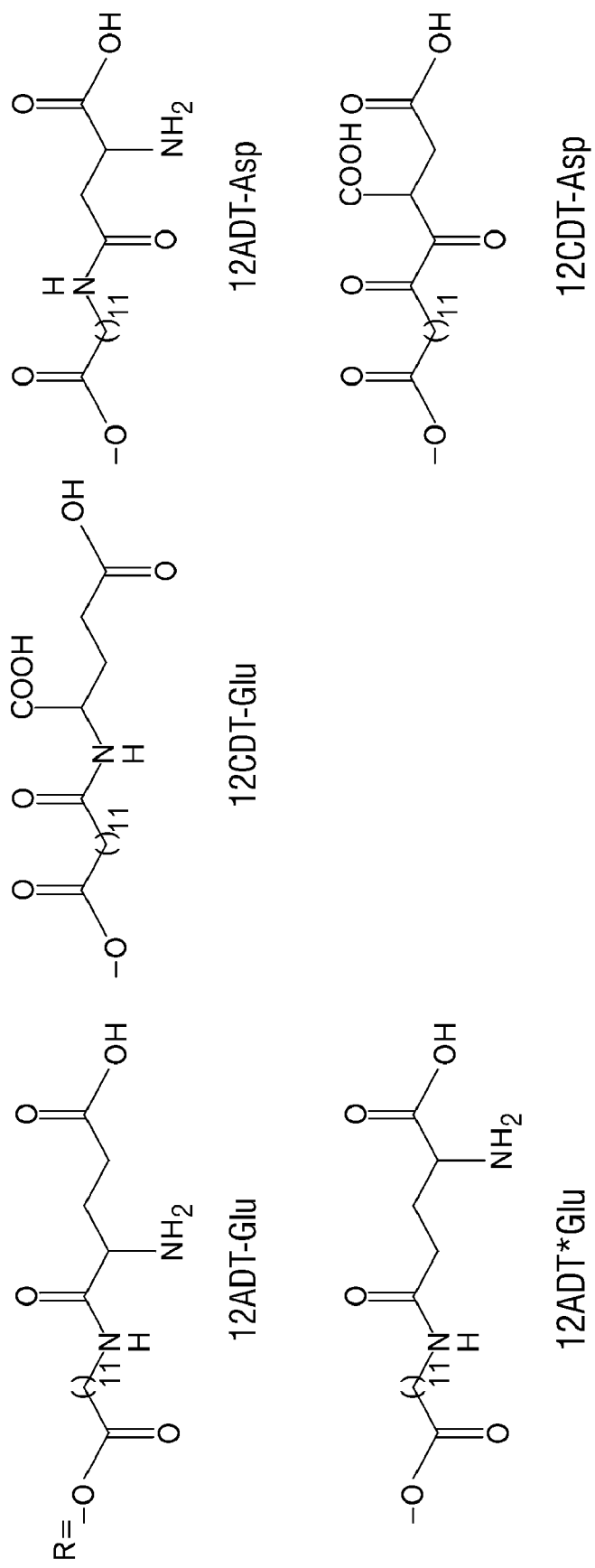
FIG. 2 is a set of structures for particular embodiments of linkers which can be linked to amine groups of therapeutic drugs.

Some preferred peptides include a PSMA-hydrolyzable, α-linked dipeptide "cap" that are not substrates for GGH, and are more specific PSMA substrates. Combination α- and side chain-linked PSMA substrates can be highly efficient and specific. For example, Glu*Glu*Glu*Asp-Glu, and Glu*Glu*Glu*Asp-Gln have high stability in serum. Peptides containing two α-linkages and two γ-linkages, for example, Asp-Glu*Glu*Asp-Glu can be completely stable to hydrolysis in human and mouse plasma. A number of aspartate- and glutamate-containing linkers are depicted in FIG. 2. These particular linkers can be bonded to amine groups on therapeutic drugs.

The peptides listed are among those that are preferred: Glu*Glu*Glu*Asp-Glu, Asp-Glu*Glu*Asp-Glu, and Glu-Glu*Glu*Asp-Glu. Numerous other peptides with mixed α- and side chain linkages and otherwise corresponding to the description herein can be readily envisioned and constructed by those of ordinary skill in the art.

The peptides of the invention are preferably not more than 20 amino acids in length, more preferably not more than 6 amino acids in length. Some peptides which are only two or three amino acids in length are quite suitable for use in the prodrugs described herein. Some preferred amino acid sequences of the invention are linear. However, multiple linkage sites present on dicarboxylic amino acids may also be used to produce branched peptides. These branched peptides could include a therapeutic agent coupled to each amino acid of the peptide chain, such that cleavage of individual amino acids from the peptide chain by the enzymatic activity of PSMA releases multiple molecules of therapeutic agent.

Further examples of the peptides of the invention are constructed as analogs of, derivatives of, and conservative variations on the amino acids sequences disclosed herein. The term "isolated" as used herein refers to a peptide substantially free of proteins, lipids, nucleic acids, for example, with which it is naturally associated. Those of skill in the art can make similar substitutions to achieve peptides with greater activity and/or specificity toward PSMA. For example, the invention includes the peptide sequences described above, as well as analogs or derivatives thereof, as long as the bioactivity of the peptide remains. Minor modifications of the primary amino acid sequence of the peptides of the invention may result in peptides which have substantially equivalent activity as compared to the specific peptides described herein. Such modifications may be deliberate, as by site-directed mutagenesis or chemical synthesis, or may be spontaneous. All of the peptides produced by these modifications are included herein, as long as the biological activity of the original peptide remains, i.e., susceptibility to cleavage by PSMA.

Further, deletion of one or more amino acids can also result in a modification of the structure of the resultant molecule without significantly altering its biological activity. This can lead to the development of a smaller active molecule which would also have utility. For example, amino or carboxy terminal amino acids which may not be required for biological activity of the particular peptide can be removed. Peptides of the invention include any analog, homolog, mutant, isomer or derivative of the peptides disclosed in the present invention, as long as the bioactivity as described herein remains. All peptides were synthesized using L-amino acids, and these amino acids are preferred; however, D-forms of the amino acids can be synthetically produced.

The peptides of the invention include peptides which are conservative variations of those peptides specifically exemplified herein. The term "conservative variation" as used herein denotes the replacement of an amino acid residue by another, biologically similar residue. Examples of conservative variations include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine, and threonine. The term "conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention with respect to X positions which may be any of a number of amino acids. The peptides which are produced by such conservative variation can be screened for suitability of use in the prodrugs of the invention according to the methods for selecting prodrugs provided herein.

The peptides of the invention can be synthesized according to any of the recognized procedures in the art, including such commonly used methods as t-boc or fmoc protection of alpha-amino groups. Both methods involve stepwise syntheses whereby a single amino acid is added at each step starting from the C-terminus of the peptide. (see, Coligan, et al, *Current Protocols in Immunology*, Wiley Interscience, 1991, Unit 9). Peptides of the invention can also be synthesized by the well-known solid phase peptide synthesis methods described in Merrifield, *J. Am. Chem. Soc.*, 85:2149, 1962), and Stewart and Young, *Solid Phase Peptide Synthesis*, (Freeman, San Francisco, 1969, pp. 27-62), using a copoly(styrene-divinylbenzene) containing 0.1-1.0 mM amine/gram polymer. Polyglutamated methotrexate was purchased from Schirks Laboratories. Other analogs were constructed using APA purchased from Sigma Chemical (St. Louis, Mo.). The peptides were synthesized with the appropriate blocking groups on the carboxyl groups, and the APA was coupled to the peptide using standard coupling chemistry. Such synthetic procedures are well known to those of ordinary skill in the art.

On completion of chemical synthesis, the peptides can be deprotected and cleaved from the polymer by treatment with liquid HF-10% anisole for about ¼ to 1 hour at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as solvent. Lyophilization of appropriate fractions of the column will yield the homogeneous peptide of peptide derivatives, which can then be characterized by such standard techniques as amino acid analysis, thin layer chromatography, high performance liquid chromatography, ultraviolet absorption spectroscopy, molar rotation, solubility, and quantitated by solid phase Edman degradation.

The invention encompasses isolated nucleic acid molecules encoding the PSMA-specific peptides of the invention, vectors containing these nucleic acid molecules, cells harboring recombinant DNA encoding the PSMA-specific peptides of the invention, and fusion proteins which include the PSMA-specific peptides of the invention. Especially preferred are nucleic acid molecules encoding the polypeptides described herein.

The PSMA-specific peptides are cleaved by PSMA to yield at least 5 picomoles, preferably at least 10 picomoles, and most preferably at least 15 picomoles of cleaved peptide per minute per milligram of PSMA. Desirably, the peptides are highly selective towards cleavage by PSMA, so that cleavage by other purified extracellular proteases is minimized. The peptides disclosed herein are cleaved by extracellular proteases other than PSMA to yield not more than 4.0 picomoles, preferably not more than 2.0 picomoles, and more preferably not more than 1.0 picomole of cleaved peptide per minute per milligram of purified extracellular non-PSMA proteases. The peptides described herein are also stable toward cleavage in sera. The peptides containing this sequence yield at most 5%, preferably at most 2.5% and more preferably at most 1.0% cleaved peptide from uncleaved peptide in human serum over a 24-hour period.

Prodrug Compositions

A wide variety of entities can be linked to the α-amino terminus, the α-carboxy terminus, or the side chain of the peptide, preferably at $X_1$, but also at any position from $X_1$ to $X_{n-1}$. In some preferred embodiments, linkage between the entities and the peptide takes place at $X_1$, at either the amino terminus, or at the side chain.

Notably, therapeutic drugs can be linked to these positions, creating prodrugs. The therapeutic drugs that may be used in the prodrugs of the invention include any drugs which can be directly or indirectly linked to the PSMA-specifically cleavable peptides of the invention. Hydrolytic processing of prodrugs by PSMA results in a final product consisting of a therapeutic drug coupled to an amino acid such as aspartate or glutamate. Preferred therapeutic drugs incorporate aspartic, glutamic acid or some other dicarboxylic acid into their structure and still maintain their therapeutic effect, for example, cytotoxicity. In this way, advantage is taken of the PSMA-specificity of the cleavage site, as well as other functional characteristics of the peptides of the invention. Preferred drugs are those that contain an acidic amino acid, for example Asp or Glu. The presence of an amino acid in the drug allows the formation of an amide bond between the drug and the peptide. This bond serves as the cleavage site for PSMA. As noted above, the peptides of the invention can be used to activate therapeutic drugs at PSMA producing tissue. The peptides which are useful in the prodrugs of the invention are those described above.

Certain therapeutic drugs contain acidic amino acids. Examples of these include methotrexate, ralitrexed (Tomudex), edatrexate, and 5,10 dideaztetrahydrofolate (Lometrexol). Other therapeutic drugs are required to have acidic amino acids introduced by chemical or biochemical synthesis, for example, sesquiterpene-γ-lactones such as those belonging to the guaianolide, inuchineolide, germacranolide, and eudesmanolide families of sesquiterpenoids. These include estafiatin, grossheimin, inuchinenolide, arglabin, thapsigargin and their derivatives, such as thapsigargicin and many others known to those skilled in the art. Thapsigargin and its derivatives are believed to act by inhibiting the SERCA pump found in many cells. Other classes of agents include acidic amino acid containing derivatives of the antifolate trimetrexate, and the anthracyclines antibiotics containing an amino sugar such as doxorubicin, daunorubicin, epirubicin (4-epidoxorubicin), idarubicin (4-demethoxydaunomycin) and the like. These drugs intercalate into polynucleotides and interfere with replication processes. An additional class of agents would include derivatives of the taxane class of agents (examples of this class are taxol and taxotere). Amino acid-containing derivatives of these agents maintain therapeutic efficacy.

Preferably, therapeutic drugs are linked to the peptide either directly or indirectly, through a linker group. The direct linkage can be made conveniently through an amide bond, for example. If therapeutic drugs are linked to the peptide through the α-amino group of $X_1$, an amide bond is conveniently created with a carboxyl present on the therapeutic drug, or with a carboxyl present on any linker. If therapeutic drugs are linked to the peptide through the side chain- or α-carboxyl of $X_1$ or any other amino acid in the peptide, an amide bond is conveniently created with an amino group present on the therapeutic drug, or with an amino group present on any linker.

The linker may be connected to the therapeutic drug through any of the bond types and chemical groups known to those skilled in the art. Therapeutic drugs can also be coupled directly to the α-amine of an amino acid of peptides via a linker.

The linker can either remain attached to the drug or be cleaved off. In embodiments in which the linker remains attached to the drug, the linker can be any group which does not substantially inhibit the non-specific toxicity of the drug after cleavage from the peptide. Suitable linkers are primary amine containing alkanoyl, alkenoyl, and arenoyl substituents. Examples of such linkers are $CO-(CH=C)_{n1}-(CH_2)_{n2}-Ar-NH_2$, $CO-(CH_2)_{n2}-(CH=CH)_{n1}-Ar-NH_2$, $CO-(CH_2)_{n2}-(CH=CH)_{n1}-CO-NH-Ar-NH_2$ and $CO-(CH=CH)_{n1}-(CH_2)_{n2}-CO-NH-Ar-NH_2$ and substituted variations thereof, where n1 and n2 are from 0 to 5, and Ar is any substituted or unsubstituted aryl group. Substituents which may be present on Ar include short and medium chain alkyl, alkanoxy, aryl, aryloxy, and alkenoxy groups, nitro, halo, and primary secondary or tertiary amino groups, as well as such groups connected to Ar by ester or amide linkages. Amino acids can also serve as linkers. A dicarboxylic acid linker can be used, such as the 12-carbon linker 12-carboxydodecanoate, shown, for example, for (12-CDT-Asp) in FIG. 2. This analog can then be linked via either the α-carboxyl or side-chain carboxyl to a longer peptide chain.

In other embodiments, the linker is self-cleaving. Self-cleaving linkers are those which are disposed to cleave from the drug after the cleavage of the peptide by PSMA. The linkers generally contain primary amines which form amide bonds to the carboxy terminus of the peptide sequence. The linkers can also contain a carboxylic acid which forms an amide bond to a primary amine found on the drug.

In such embodiments, the linker is not required to be non-interfering with the non-specific toxicity of the drug, as long as it is cleaved within a period of time short enough to allow the drug to remain localized where it has been activated, or within a period of time short enough to prevent inactivation by any means.

The linker may remain on the therapeutic drug indefinitely after cleavage, or may be removed soon thereafter, either by further reactions with external agents, or in a self-cleaving step. Self-cleaving linkers are those linkers which can intramolecularly cyclize and release the drug, or undergo spontaneous $S_N1$ solvolysis and release the drug upon peptide cleavage. Such linkers are for example 2,2-dialkyl-2-(2-anisyl) acetic acid, described in Atwell et al., *J. Med. Chem.*, 37:371-380, (1994), and p-amidobenzyloxycarbonyl, described in Carl et al., *J. Med. Chem.*, 24:479-480, (1981). Further useful examples are provided in these references. Other materials such as detectable labels or imaging compounds can be linked to the peptide. Groups can also be linked to the carboxy side chains of $X_1$ to $X_{n-1}$, including such moieties as antibodies, and peptide toxins, including the 26 amino acid toxin, melittin and the 35 amino acid toxin, cecropin B, for example. Both of these peptide toxins have shown toxicity against cancer cell lines.

FIG. 1 is a structure of a particular embodiment of a PSMA-activated TG prodrug. DBTG refers to 8-O-debutanoylthapsigargin, which is linked via the oxygen atom to the remainder of the prodrug as shown. The portion of the molecule labeled as E*12-ADT is the 12-amino dodecanoate side chain. Thus, preferred substrates combine the specificity of the α-linkage with the enhanced efficiency of the γ-linkage. The longer-length, negatively-charged, substrates can serve two additional purposes: first, they help to make highly lipophilic toxins, for example, TG analogs, more water soluble; second, the highly charged prodrug will be less likely to cross the plasma membrane, further limiting non-specific cytotoxicity.

The following prodrugs are particularly preferred:

(1) 12ADT-Glu*Glu*Glu*Asp-Glu (4)12ADT-Asp-Glu*Glu*Asp-Glu (2) 12ADT*Glu-Glu*Glu*Asp-Glu (5) 12CDT-Asp-Glu*Glu*Asp-Glu (3) 12CDT-Glu*Glu*Glu*Asp-Glu

The prodrugs are hydrolyzed by PSMA and release the corresponding Asp- or Glu-containing TG analogs or the TG analog itself, and also lack potent cytotoxicity when not metabolized by PSMA. Non-PSMA producing TSU-Pr1 human prostate cancer cell line is exposed to each of the prodrugs at doses that are approximately 50-times the $LD_{50}$ for the corresponding free TG analog. Against the TSU prostate cancer cell line, 12ADT-Glu has an $LD_{50}$ value for killing of ~50 nM.

The prodrugs are hydrolyzed by PSMA and have a dose-responsive ability to kill PSMA-producing LNCaP and CWR22R cells in vitro, based upon loss of clonogenic abilities. The activity of these cell lines is approximately 13 pmoles NAAG hydrolyzed/min/mg protein for LNCaP and approximately 20 pmoles NAAG hydrolyzed/min/mg protein for CWR22R cells, using radiolabeled $^3$H-NAAG. These prodrugs are tested against TSU cells that have been transduced with a lentiviral vector carrying the PSMA gene. This TSU-PSMA cell line produces amounts of PSMA that are similar to LNCaP as determined by Western Blot. The activity of the PSMA from this line is comparable to the LNCaP and CWR22R lines (that is, approximately 18 pmoles NAAG hydrolyzed/min/mg protein). This TSU-PSMA line is used to determine the therapeutic index by comparing cytotoxic activity of the prodrugs against this PSMA-producing line and the wild type TSU cells. Using these data, $LD_{50}$ values for all the tested compounds is calculated. To be considered selective, the preferred prodrugs have a >20-fold difference in ability to kill TSU-PSMA vs. TSU wild type cells.

The prodrugs of the invention are not taken up by the cells, but are cleaved extracellularly by PSMA to yield at least 5 picomoles, preferably at least 10 picomoles, and more preferably at least 15 picomoles of therapeutic drug per minute per milligram of PSMA. Preferably, the prodrugs of the invention are cleaved by extracellular proteases other than PSMA to yield not more than 4.0 picomoles, preferably not more than 2.0 picomoles, and more preferably not more than 1.0 picomole of therapeutic drug per minute per milligram of purified extracellular non-PSMA proteases. The prodrugs of the invention yield at most 5%, preferably at most 2.5%, and more preferably at most 1.0% of prodrug as therapeutic drug in human serum over a 24-hour period.

The prodrugs of the invention may also comprise groups which provide solubility to the prodrug as a whole in the solvent in which the prodrug is to be used. Most often the solvent is water. This feature of the invention is important in the event that neither the peptide nor the therapeutic drug is soluble enough to provide overall solubility to the prodrug. These groups include polysaccharides or other polyhydroxylated moieties. For example, dextran, cyclodextrin, starch and derivatives of such groups may be included in the prodrug of the invention.

Methods of Treatment Using Prodrugs

The invention also provides methods of treating PSMA-producing cell proliferative disorders of the invention with the prodrugs of the invention. Hydrolytic processing of prodrugs by PSMA results in a final product consisting of a therapeutic drug or a therapeutic drug coupled to an amino acid such as aspartate or glutamate. Preferred therapeutic drugs incorporate aspartic, glutamic acid or some other dicarboxylic acid into their structure and still maintain their therapeutic effect. Prodrugs can be tested for cytotoxicity against PSMA-producing LNCaP, CWR22R and the TSU-PSMA and wild type TSU human cancer cells.

The prodrugs of the invention and/or analogs or derivatives thereof can be administered to any host, including a human or non-human animal, in an amount effective to treat a disorder.

The prodrugs of the invention can be administered parenterally by injection or by gradual infusion over time. The prodrugs can be administered intravenously, intraperitoneally, intramuscularly, subcutaneously, intracavity, or transdermally. Preferred methods for delivery of the prodrug include intravenous or subcutaneous administration. Other methods of administration will be known to those skilled in the art.

Preparations for parenteral administration of a prodrug of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases, and the like.

The term "cell-proliferative disorder" denotes malignant as well as non-malignant cell populations which often appear to differ from the surrounding tissue both morphologically and genotypically. Malignant cells (i.e. cancer) develop as a result of a multistep process. The PSMA-specific prodrugs of the invention are useful in treating malignancies of the various organ systems. Essentially, any disorder which is etiologically linked to PSMA expression could be considered susceptible to treatment with a PSMA-specific prodrug. One such disorder is a malignant cell proliferative disorder, for example. Malignant PSMA-producing cell proliferation disorders include breast cancer, pancreatic cancer, brain cancer, melanoma, lung cancer, testicular cancer and sarcoma. The term "therapeutically effective amount" as used herein for treatment of cell proliferative disorders refers to the amount of prodrug sufficient to cause a reduction in the number of unwanted cells. The term "therapeutically effective" therefore includes the amount of prodrug sufficient to prevent, and preferably reduce by at least 25%, and more preferably to reduce by 90%, the number of unwanted cells. The dosage ranges for the administration of prodrug are those large enough to produce the desired effect. Generally the dosage will vary with age, condition, sex, and extent of the disorder in the subject, and can be determined by one skilled in the art. The dosage can be adjusted by the individual physician in the event of any contraindications. In any event, the effectiveness of treatment can be determined by monitoring tumor ablation.

Method of Producing Prodrugs

The invention, in another aspect, provides a method of producing the prodrugs of the invention. This method involves linking a therapeutically active drug to a peptide of the invention. Such peptides are described above. After the drug and peptide are linked to produce a therapeutic prodrug composition, the non-specific toxicity of the drug is substantially inhibited. In certain embodiments, the peptide is linked directly to the drug. In other embodiments, the peptide is indirectly linked to the drug, the linkage occurring through a linker. In each case the amino terminus of the peptide is used for linking. The drug can be linked to the α-amine of the amino terminal amino acid or it can be linked to a carboxyl side-chain of an acidic amino acid at the amino terminus of the peptide, or at any position from $X_2$ to $X_{n-1}$, except when n is 2. That is, in an amino acid sequence $X_1 X_2 \ldots X_n$, the link is established through $X_1$ or $X_2$ to $X_{n-1}$, preferably through $X_1$. The therapeutic drug can contain a primary amine group or a carboxyl group to facilitate the formation of an amide bond with the peptide. Many acceptable methods of coupling carboxyl and amino groups to form amide bonds are known to those of skill in the art.

The bonds of the amino acids in the peptide are sequentially cleaved by PSMA, releasing the therapeutic drug. Suitable linkers include any chemical group which contains a primary amine or carboxyl group. The linkers for use in the present invention include amino acids, primary amine- or carboxyl-containing alkyl, alkenyl or arenyl groups.

The connection between the linker and the therapeutic drug may be of any type known in the art, preferably covalent bonding. The linker group may remain attached to the therapeutic drug if its attachment does not significantly reduce the non-specific toxicity of the drug. In certain embodiments, the linker is a cleavable linker, which may be cleaved either by an external agent, or it may be a self-cleaving linker. External agents which may effect cleavage of the linker include enzymes, proteins, organic or inorganic reagents, protons and any other agents which do not affect the non-specific toxicity of the drug or prodrug.

In certain embodiments, the linker comprises an amino acid sequence. The sequence may be of any length, but is preferably between 1 and 10 amino acids, most preferably between 1 and 5 amino acids in length. Preferred amino acids are glutamate, aspartate, glutamine, asparagine, or amino acid sequences containing these amino acids, especially at their amino termini, although conservative variations of these amino acids may also be utilized. More preferably, the linker includes glutamate or aspartate.

Other groups may be added to the prodrugs of the invention, including those which render the prodrug soluble in water. These groups include polysaccharides or other polyhydroxylated moieties. For example, dextran, cyclodextrin and starch may be included in the prodrug of the invention.

Method of Screening Tissue

In another aspect the invention provides a method of detecting PSMA-producing tissue using the peptides of the invention, as described above. The method is carried out by contacting a detectably labeled peptide of the invention with target tissue for a period of time sufficient to allow PSMA to cleave the peptide and release the detectable label. The detectable label is then detected. The level of detection is then compared to that of a control sample not contacted with the target tissue. Many varieties of detectable label are available, including optically based labels, such as chromophoric, chemiluminescent, fluorescent or phosphorescent labels, and radioactive labels, such as alpha, beta or gamma emitting labels. Examples of fluorescent labels include amine-containing coumarins such as 7-amino-4-methylcoumarin, 7-amino-4-trifluoromethyl, and other amine-containing fluorophores such as 6-aminoquinoline, and rhodamines, including rhodamine 110. Other examples of fluorescent labels include those containing carboxyl moieties such as FITC. Examples of radioactive labels include beta emitters such as $^3H$, $^{14}C$ and $^{125}I$. Examples of chromophoric labels (those that have characteristic absorption spectra) include nitroaromatic compounds such as p-nitroaniline. Examples of chemiluminescent labels include luciferins such as 6-amino-6-deoxyluciferin.

Preferably, the choice of detectable label allows for rapid detection and easily interpretable determinations. Detectable labels for use in the invention preferably show clearly detectable differences between detection from the cleaved and uncleaved state.

The invention provides a method for detecting a cell proliferative disorder which comprises contacting a PSMA-specific peptide with a cell suspected of having a PSMA-production associated disorder and detecting cleavage of the peptide. The peptide reactive with PSMA is labeled with a compound which allows detection of cleavage by PSMA. For purposes of the invention, a peptide specific for PSMA may be used to detect the level of enzymatically active PSMA in cell membranes, and potentially in saliva, blood, or urine. Any specimen containing a detectable amount of antigen can be used. The level of PSMA in the suspect cell can be compared with the level in a normal cell to determine whether the subject has a PSMA-production associated cell proliferative disorder. Preferably the subject is human.

Method of Screening Prodrugs

The invention also provides a method of selecting potential prodrugs for use in the invention. The method generally consists of contacting prodrugs of the invention with PSMA-producing tissue and non-PSMA producing tissue in a parallel experiment. "PSMA-producing tissue" as used herein is tissue that produces at least 1 ng enzymatically active PSMA per gram of tissue, or at least 1 ng of enzymatically active PSMA/$10^6$ cells/24 hours from cells. The prodrugs which exert toxic effects in the presence of PSMA-producing tissue, but not in the presence of non-PSMA producing tissue are suitable for the uses of the invention. In other words, the $LC_{50}$ concentration of the prodrug in the presence of PSMA-producing tissue is at least 3 times lower, more preferably at least 20 times lower, and most preferably at least 100 times lower than the $LC_{50}$ concentration of the prodrug in the presence of non-PSMA producing tissue.

Method of Determining PSMA Activity

The invention also provides a method of determining the activity of PSMA. The method generally consists of contacting detectably labeled prodrugs of the invention with samples may come from fluid drawn from PSA-producing tissue, from tissue culture media, from serum, saliva or urine, or any source which contains PSMA. The cleavage of peptide which takes place by PSMA results in the release of a detectable label, which is subsequently detected. This detection level is compared to the detection level which is found upon performing a parallel experiment in which the PSMA-containing sample is a standard solution made up from purified PSMA as described, for example, in Lapidus et al, *Prostate*, (2000) 45:350-354. This comparison results in a determination of the activity of the PSMA which is present in the sample, given a correction for any differences in PSMA concentration which may exist. Such correction may be accomplished directly by adjusting the concentrations of the standard and sample solutions to match each other or by mathematical correction means.

Method of Imaging Tissue

The invention in another aspect, provides a method of imaging soft tissue or bone metastases by providing peptides of the invention linked to lipophilic imaging labels that can be detected by imaging techniques, for example, positron emission tomography (PET). This method is accomplished generally by administering a peptide of the invention linked to a primary amine-containing lipophilic label to a subject having or suspected of having a PSMA-producing associated cell proliferative disorder. The peptide is selectively cleaved from the lipophilic imaging label where enzymatically active PSMA occurs in the subject (i.e., PSMA producing tissues). The lipophilic imaging label is then drawn into the membranes of cells in the vicinity. After a period of time sufficient to allow cleavage of the peptide by PSMA, and to allow the uncleaved peptide to be sufficiently cleared from the subject to allow reliable imaging, the subject is imaged. The lipophilic label accumulates in the soft tissue or bone that produces PSMA, and allows a diagnosis of the subject. Suitable labels for PET scanning are radionuclides such as $^{18}F$, $^{11}C$, $^{13}N$ and $^{15}O$, and any other positron emitters known in the art. Lipophilicity can be engineered into the label by introducing the label into lipophilic fragments or moieties known to those in the art, by methods known to those skilled in the art.

The invention will be further described in the following examples, which do not limit the scope of the invention described in the claims.

EXAMPLES

The following examples illustrate the preparation and properties of certain embodiments of the invention.

Example 1

Determination of PSMA Hydrolysis of Peptides

The extent to which various peptide substrates are hydrolyzed by PSMA was determined by synthesizing a series of methotrexate analogs including the 4-N[N-2,4-diamino-6-pteridinyl-methyl)-N-methylamino-benzoate] (APA) portion of methotrexate coupled to a variety of peptides. Polyglutamated methotrexate is available from Schirks Laboratories in Jona, Switzerland. The coupling of APA to the N-terminal amine of γ-linked polyglutamates does not inhibit sequential PSMA hydrolysis.

A series of α-linked peptides were investigated for PSMA hydrolysis. The results are shown in Table 1. The table shows the percentage of α-linked methotrexate analogs hydrolysed to methotrexate after being incubated with PSMA for 24 hours and for 48 hours. In Tables 1-3, to simplify identification of the type of amino acid linkages employed, α-linkages are denoted by a hyphen (for example, Glu-Glu) and all side-chain linkages are denoted by a star (for example, Glu*Glu).

TABLE 1

Methotrexate Analogs Hydrolyzed by PSMA (α-linked)

| Methotrexate Analog | % hydrolysis after 24 hours | % hydrolysis after 48 hours |
|---|---|---|
| APA-Glu-Glu | 0.0 | 0.0 |
| APA-Glu-Glu-Glu | 0.0 | 0.0 |
| APA-Asp | 0.0 | 0.0 |
| APA-Glu-Asp | 0.0 | 0.0 |
| APA-Asp-Glu | 21.5 | 45.6 |
| APA-Glu-Gln | 0.0 | 0.0 |
| APA-Asn-Glu | 0.0 | 0.0 |
| poly*Glu | 96.1 | 100 |

Substrate specificity for the pteroyl poly-γ-glutamyl carboxypeptidase (folate hydrolase) activity of PSMA was determined by synthesizing a series of γ-linked methotrexate analogs and assaying them for hydrolysis by PSMA. These results are shown in Table 2.

TABLE 2

Methotrexate Analogs Hydrolyzed by PSMA (γ-linked)

| Methotrexate Analog | % hydrolysis after 24 hours | % hydrolysis after 48 hours |
|---|---|---|
| APA-Glu*Asp | 38.3 | 84.6 |
| APA-Glu*Asp*Glu | 37.8 | 85.5 |
| APA-Glu*dGlu | 0.0 | 0.0 |
| APA-Glu*Gln | 48.2 | |
| APA-Glu*GABA | 0.0 | 0.0 |
| APA-Glu*Glu*Glu*Glu*Asp | 40.9 | 77.7 |
| poly*Glu | 96.1 | 100 |

In Table 2, GABA is gamma aminobutyric acid. The poly-Glu is all γ-linked in each of Tables 1 and 2.

In order that the prodrugs can be administered systemically via the blood, their stability in sera must be sufficiently high to avoid hydrolysis or other degradative processes which may occur prior to the prodrugs reaching their target tissues. In addition to GGH activity, a human blood plasma glutamate carboxypeptidase (PGCP) that has significant sequence homology to PSMA and glutamate carboxypeptidase activity has been identified. Therefore, to assay hydrolysis by GGH and other serum carboxypeptidases like PGCP, the APA-Glu*Glu*Glu*Glu*Asp, APA-Glu*Glu*Glu*Glu*Gln, and APA-Glu*Glu*Glu*Glu*Glu substrates were incubated in human and mouse plasma and hydrolysis determined by HPLC analysis after an 18-hour incubation, as shown in Table 3. As noted, GGH efficiently hydrolyzes poly-γ-glutamate chains as well as poly-γ-glutamated folate and methotrexate. GGH, however, is unable to hydrolyze α-linked peptides. An α-linked analog that was found to be hydrolyzable by PSMA, APA-Asp-Glu, was tested for stability in human serum, as shown in Table 3.

In Tables 1-3, to simplify identification of the type of amino acid linkages employed, α-linkages are denoted by a hyphen (for example, Glu-Glu) and all side-chain linkages are denoted by a star (for example, Glu*Glu). The column labeled "% PSMA Hydrolysis" refers to the percentage of hydrolysis of a substrate to APA-Asp or to APS-Glu by purified PSMA. The column labeled "% APA-Asp or -Glu" refers to the percentage of hydrolysis of substrate to APA-Asp or APA-Glu. The column labeled "% Prodrug Remaining" refers to the area of the HPLC peak attributable to starting material divided by the areas of HPLC peaks attributable to starting material, intermediate products, and final products. The hydrolysis of substrates in mouse plasma did not display any peaks attributable to intermediate products, but only showed starting material and APA-. "ND" means "not determined," in that the experiment was not performed.

As shown in Table 3, the side chain-linked dipeptides APA-Glu*Asp and APA-Glu*Gln were significantly hydrolyzed by PSMA. The peptides APA-Glu*Glu*Glu*Glu*Asp and APA-Glu*Glu*Glu*Glu*Gln, containing a γ-linked Asp or Gln were both hydrolyzed by PSMA to yield APA-Glu (that is, methotrexate) to a greater extent after 24 hours than any of the γ-linked dipeptide analogs. These analogs, however were less efficient substrates when compared to APA-Glu*Glu*Glu*Glu*Glu, the polyglutamated methotrexate analog with similar γ-glutamyl chain length, as shown in Table 3.

For APA-Glu*Glu*Glu*Glu*Asp, APA-Glu*Glu*Glu*Glu*Gln, and APA-Glu*Glu*Glu*Glu*Glu, >75% of the starting material was hydrolyzed to methotrexate or to other intermediate length species, consistent with sequential hydrolysis by the exopeptidase activity of GGH present in human serum, as shown in Table 3. In mouse plasma, approximately 60-75% conversion of each analog directly to APA-Glu (that is, methotrexate) was observed after 18 hours, as shown in Table 3. The addition of p-hydroxymer-

TABLE 3

Hydrolysis of PSMA Substrates by Purified PSMA and Stability in Plasma

| Substrate | % PSMA hydrolysis 24 h | % PSMA hydrolysis 48 h | 18 hour Incubation in Human Plasma % APA-Glu or -Asp | 18 hour Incubation in Human Plasma % Prodrug Remaining | 18 hour Incubation in Mouse Plasma % APA-Glu or -Asp |
|---|---|---|---|---|---|
| α-linked | | | | | |
| APA-Asp-Glu | 70 | 99 | 1 | 99 | ND |
| APA-Glu-Glu | 0 | 20 | ND | ND | ND |
| γ-linked | | | | | |
| APA-Glu*Glu*Glu*Glu*Asp | 98 | 100 | 9 | 20 | 72 |
| APA-Glu*Glu*Glu*Glu*Gln | 97 | 100 | 6 | 26 | 62 |
| APA-Glu*Glu*Glu*Glu*Glu | 96 | 100 | 11 | 11 | 68 |
| α-, γ-linked | | | | | |
| APA-Glu*Glu*Glu*Asp-Glu | 30 | 65 | 23 | 57 | 5 |
| APA-Glu*Glu*Glu*Asp-Gln | 5 | 10 | 13 | 76 | ND |
| APA-Asp-Glu*Glu*Asp-Glu | 36 | 77 | 0 | 100 | 2 | curibenzoate, a non-specific inhibitor of GGH and other cysteine proteases, resulted in complete inhibition of hydrolysis.

After an 18 hour incubation in human serum, HPLC analysis demonstrated no significant hydrolysis of the dipeptide APA-Asp-Glu, suggesting the inability of serum GGH and other serum carboxypeptidases like PGCP to cleave alpha-linked acidic peptides.

Example 2

Preparation of Thapsigargin Analogs

The starting material for all the synthesized analogs is 8-O-debutanoylthapsigargin, which is easily available by triethylamine catalyzed methanolysis of thapsigargin. Removal of the butanoyl results in loss of cytotoxic activity with an $LD_{50}$ of >50 µM compared to <100 nM for thapsigargin. Anhydrides of dicarboxylic acids of various lengths afforded analogs in which the acyl group attached to the O-8 ended in a free carboxylic acid. A dicyclohexylcarbodiimide (DCCI) promoted coupling of a 2,4-diaminoarene to the carboxylic acid analogs affords the derivatives in which contain a primary aromatic amine as a potential coupling point for additional moeities.

Another type of thapsigargin derivative has been prepared by reacting 8-O-debutanoylthapsigargin with a 4-aminophenyl aliphatic carboxylic acid like 4-aminocinnamic acid, 3-(4-aminophenyl) propionic acid, or 4-(4-aminophenyl)butanoic acid in the presence of DCCI and 4-dimethylaminopyridine. The aromatic amino group had previously been coupled to a boc-protected-amino acid like glutamine or leucine by standard techniques. After deprotection of the amino group by standard techniques the thapsigargin derivative can be coupled to the peptide.

The synthesis of thapsigargin analogs was performed generally as follows. Unless otherwise stated all reactions were performed at room temperature, and the mixtures filtered and concentrated in vacuo with column chromatography performed over silica gel 60, (0.040-0.063, Merck). Each structure was further proven by $^{13}C$ and $^1H$ NMR spectroscopy and mass spectrometry. The NMR spectra have been recorded on an AF200X Bruker spectrometer in deuterated solutions using tetramethylsilane as an internal standard. In all the spectra, the signal originating in the acetyl, angeloyl, butanoyl, and octanoyl residues have been found as previously reported (Christensen, et al. *Phytochemistry.* 23: 1659-63, (1984)), and are not reported. The $^1H$ NMR spectra were recorded at 200 MHz. The signals of H-9' have, in many cases, been overlapped by signals from the protons in the octanoyl residue. The $^{13}C$ NMR spectra were recorded at 50 MHz. In the $^{13}C$ NMR spectra the assignments of signals with similar chemical shift values might be interchanged. The signals originating in C-2 and C-6 are hidden by the signals of chloroform, but have been visualized in a few cases by recording the DEPT spectra. The small amounts of compounds available have in some cases precluded the observation of signals of poor intensities.

Figure 3:
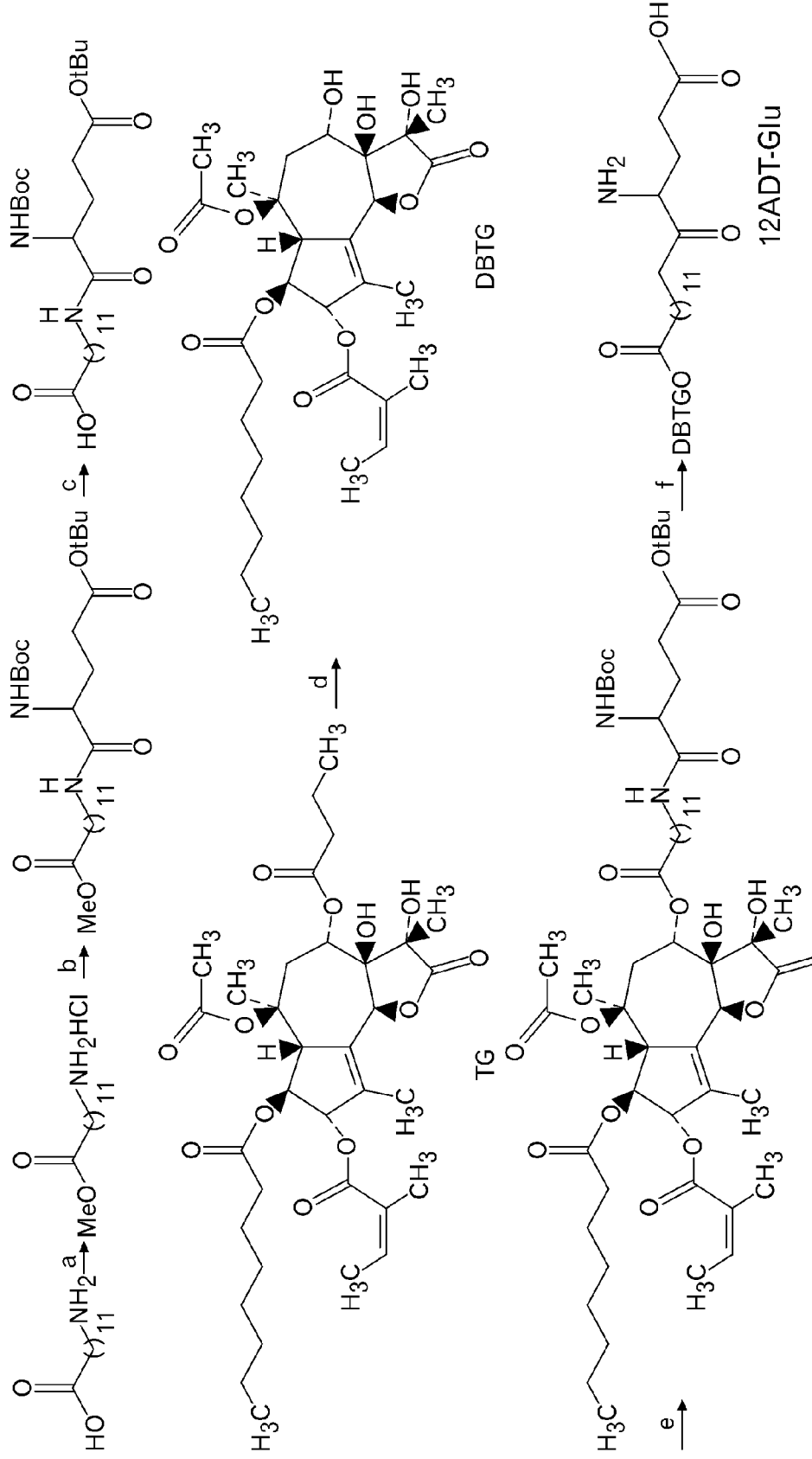
FIG. 3 is a schematic diagram for the synthesis of aspartate- and glutamate-containing thapsigargin analogs, with the synthesis of 12-ADT-Glu (8-O-(12-[L-glutamylamino]-dodecanoyl)-8-O-debutanoylthapsigargin) illustrated as an example of the method.

FIG. 3 shows a general synthetic scheme for the production of the title compounds of this example. On of the ordinary skill in the art of organic synthesis, particularly peptide synthesis, will recognize the abbreviations given for various reagents, and will also readily be able to derive appropriate reaction conditions, in light of not only the knowledge and abilities of one of ordinary skill in the art, but also of the more detailed procedures given herein.

A glutamate-containing TG analog, 12ADT-Glu, has been synthesized according to the synthetic method outlined in FIG. 3. According to the reactions illustrated in the synthetic method of FIG. 3, DIPEA is diisopropylethylamine, DCCI is dicyclohexylcarbodiimide, DMAP is 4-dimethylaminopyridine, and TFA is trifluoroacetic acid.

The TG analog was synthesized by coupling the primary amine of 12ADT to the γ-carboxyl of glutamate, leaving the α-carboxyl of glutamate free to link to other amino acids, as shown in FIG. 2. The 12-ADT*Glu is a potent, cell-proliferation independent inducer of the apoptotic death of prostate cancer cells ($LD_{50}$ is approximately 50 nM). The corresponding analog consisting of 12-ADT linked to the α-carboxyl of glutamate (that is, 12ADT-Glu) is also a suitable analog, as shown in FIG. 2. The prodrug containing 12ADT*Glu coupled to the longer amino acid chain (that is, 12ADT*Glu-Glu*Glu*Asp-Glu) can also be a suitable substrate. The 12ADT-Glu*Glu*Glu*Asp-Glu prodrug may also be cleaved by PSMA, which may cleave the last peptide bond in the absence of a free α-carboxyl. TG can be coupled directly to the amine of glutamate via a 12-carbon dicarboxylic acid linker (12CDT-Glu), as shown in FIG. 2, to provide a further useful substrate. This analog can then be linked via either the α- or γ-carboxyl to a peptide chain.

Example 3

Preparations of N-L-leucyl-6-aminohexanoyl-, N-L-leucyl-12-amino dodecanoyl-, N-D-leucyl-12-amino dodecanoyl-, and N-L-alanyl-12-amino dodecanoyl-8-0-debutanoylthapsigarins (L-6-AHT, L-12-ADT, LD-12-ADT and A-12-ADT)

Figure 5:
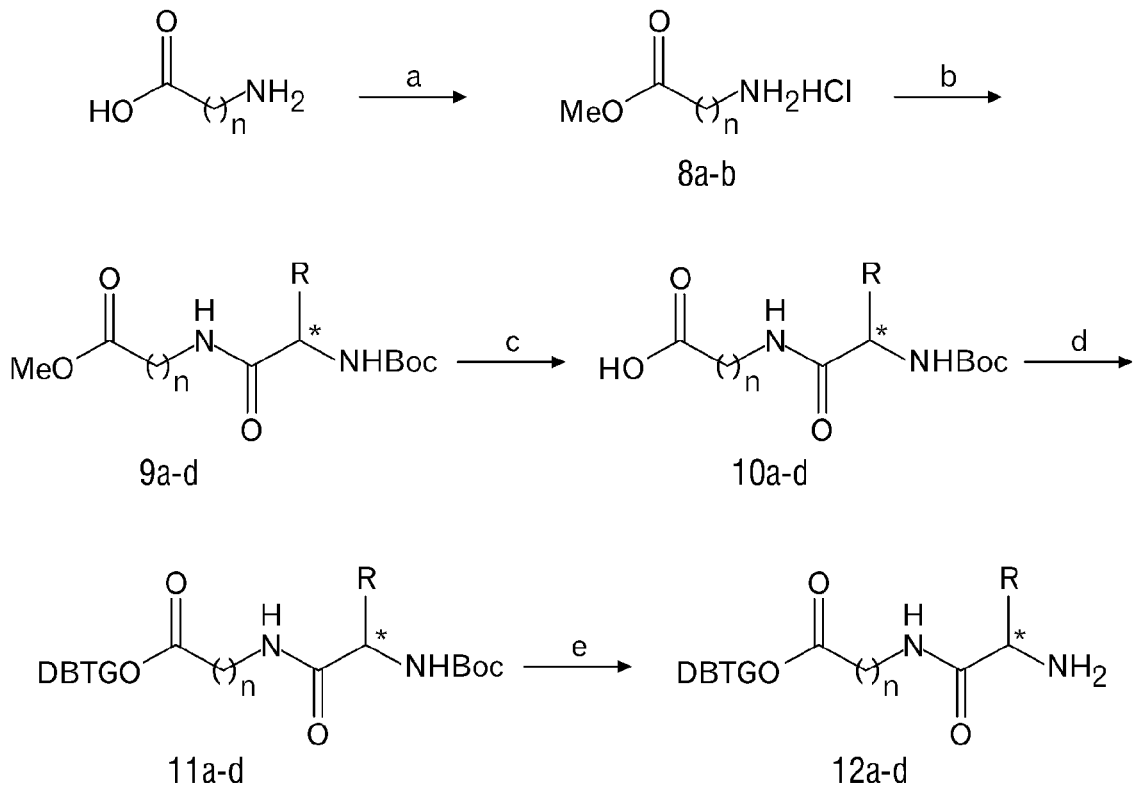
FIG. 5 is a scheme of the syntheses of particular thapsigargin analogs (leucine-containing alkanoyl thapsigargins).

FIG. 5 shows a general synthetic scheme for the production of the title compounds of this example. On of the ordinary skill in the art of organic synthesis, particularly peptide synthesis, will recognize the abbreviations given for various reagents, and will also readily be able to derive appropriate reaction conditions, in light of not only the knowledge and abilities of one of ordinary skill in the art, but also of the more detailed procedures given herein.

Example 4

Preparation of N-L-γ-glutamyl-12-aminododecanoyl-8-0-debutanoyl Thapsigargin (EG-12-ADT)

Figure 6:
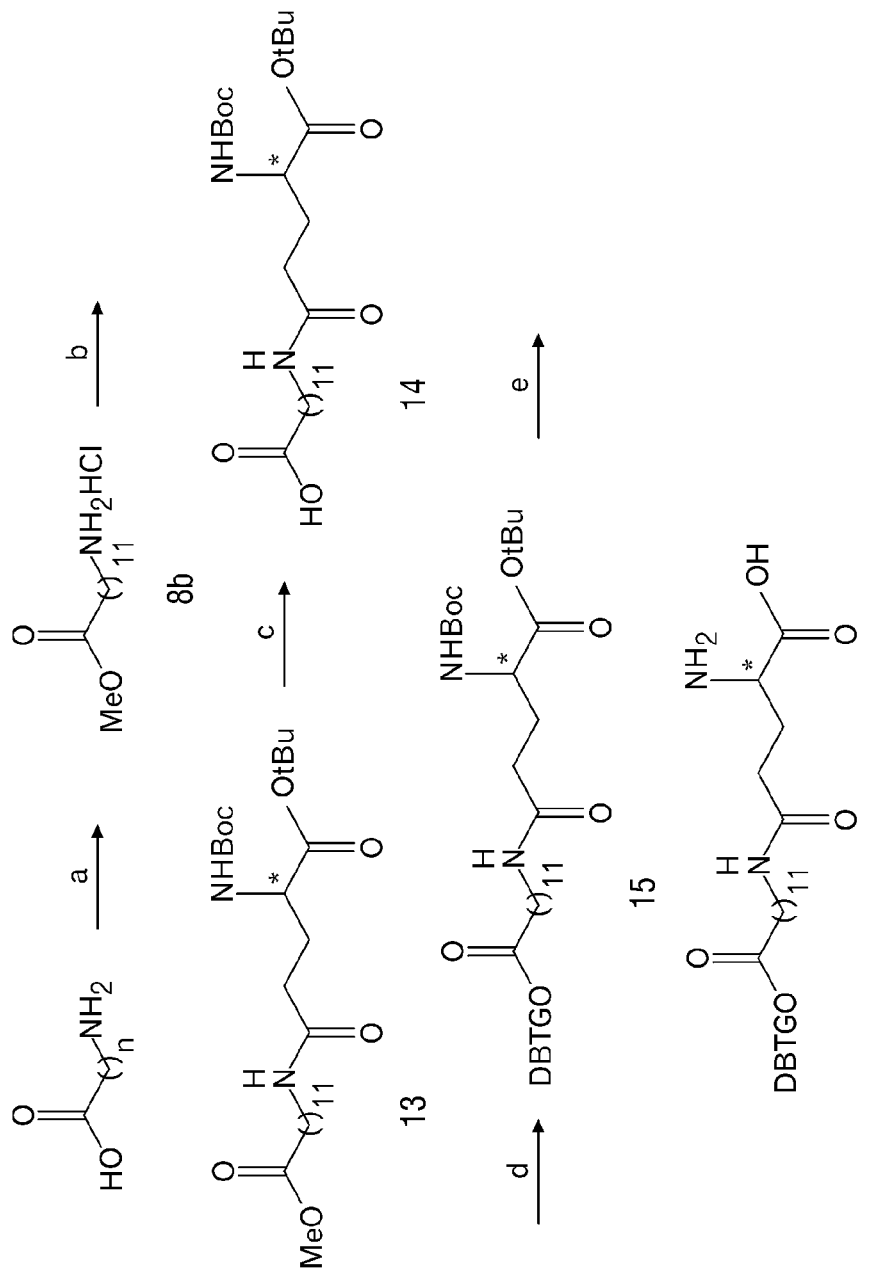
FIG. 6 is a scheme of the syntheses of particular thapsigargin analogs (glutamic acid-containing alkanoyl thapsigargins).

FIG. 6 shows a general synthetic scheme for the production of the title compound of this example. On of the ordinary skill in the art of organic synthesis, particularly peptide synthesis, will recognize the abbreviations given for various reagents, and will also readily be able to derive appropriate reaction conditions, in light of not only the knowledge and abilities of one of ordinary skill in the art, but also of the more detailed procedures given herein.

Example 5

In Vivo Administration of Prodrugs

The in vivo administration of the prodrugs described herein is initially carried out in athymic nude mice (n=3/group), which will receive increasing doses of prodrug subcutaneously daily for 5 days to determine tolerable doses for tumor efficacy studies. Additional animals are given similar doses intravenously to further determine toxicity.

Athymic nude mice are inoculated subcutaneously with TSU-PSMA cells. In one set of experiments, tumor-bearing animals (n=10/group) are given prodrug subcutaneously with tumor volume measured twice weekly and compared to vehicle treated tumor-bearing controls. Animals are treated with prodrugs daily×5 for a period of 4 weeks or until toxicity or until tumors are >2 cc. At the end of each experiment, animals are euthanized and tumors recovered and weighed. Toxicity is assessed twice weekly by visual inspection and body weights. Animals that lose >15% body weight are sacrificed. To assess specificity of PSMA-mediated prodrug hydrolysis, a second set of experiments on animals is performed, in which animals are inoculated in one flank with TSU-PSMA cells and simultaneously inoculated in the opposite flank with wild type TSU cells. These animals are then treated with prodrug to determine if non-specific activation by the wild type tumor cells is occurring. Prodrugs that are active against TSU-PSMA are then tested for efficacy against other PSMA-producing human prostate cancer xenografts (that is, LNCaP and CW22R).

To assay the products of PSMA and/or non-specific hydrolysis of the TG prodrugs in vivo, prodrugs are labeled using [$^3$H], as described in Christensen et al., *Bioorg. Medicinal Chemistry*, 7:1273-80, (1999). HPLC separation of proteolytic products is performed by injecting samples onto a C-18 reverse phase column and gradient eluted with increasing concentrations of acetonitrile/0.1% TFA. The tritiated [$^3$H] TG analog coupled products are detected by an inline radioactive flow detector and by monitoring absorbance at 215 nm. In this way mice are injected with radiolabeled prodrug, and at various time points animals are sacrificed. Extracts from serum, PSMA-positive tumors, and organs such as liver, kidney, and spleen are made. These extracts are analyzed by HPLC with inline radioactive flow to determine presence of the free TG analog and TG analog coupled to peptide. These results are used to guide additional dosing studies.

Example 6

Selectivity of a PSMA-Targeted Prodrug

Figure 4:
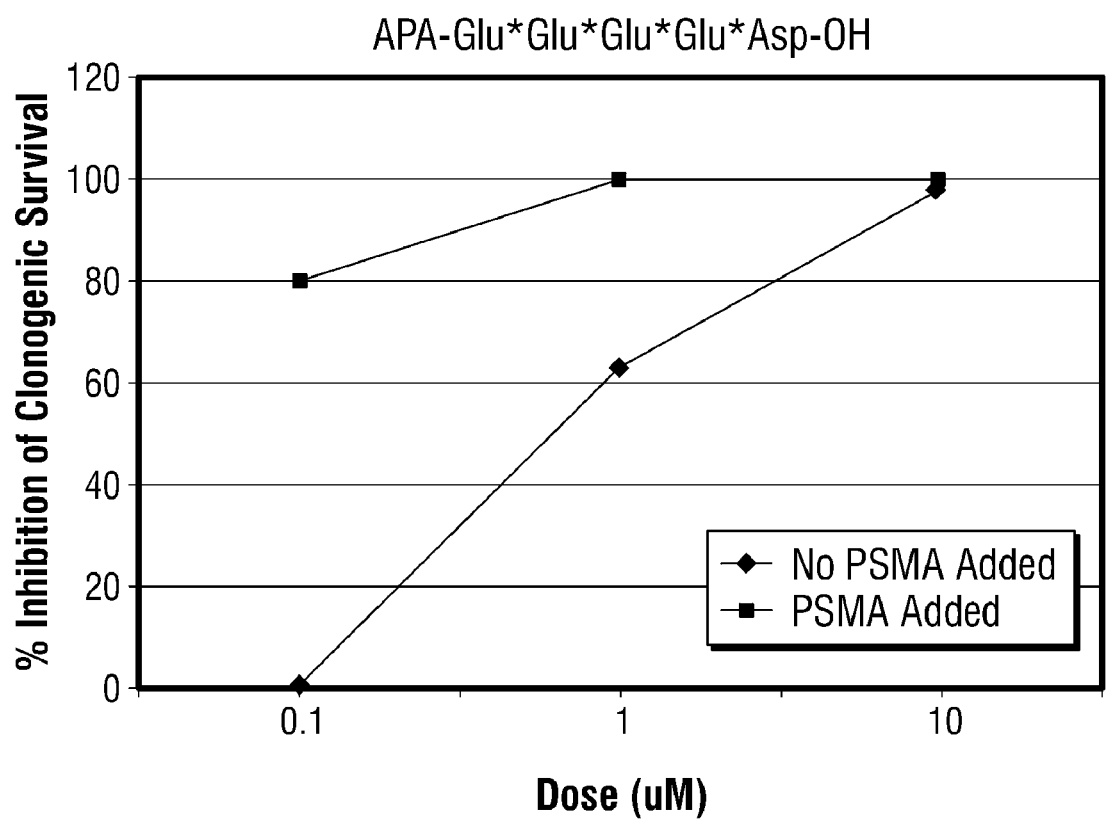
FIG. 4 is a graph of the percentage inhibition of clonogenic survival of TSU cells exposed to various concentrations of APA-Glu*Glu*Glu*Glu*Asp in the presence or absence of PSMA.

The methotrexate analog sequence APA-Glu*Glu*Glu*Glu*Asp was contacted with the non-PSMA producing TSU cancer cell line in various amounts. Exogenous PSMA (10 micrograms/mL) was added to the media and the percent inhibition of clonogenic survival was monitored. The results are shown in FIG. 4. FIG. 4 shows that there is selectivity of this methotrexate analog sequence.

Example 7

Toxicity of Methotrexate Analogs

A number of methotrexate analogs were studied for their effect on clonogenic survival of TSU cancer cells. One such analog is L-aspartic acid, N-[4-[[(2,4-diamino-5-ethyl-6-quiazolinyl)methyl]amino]benzoyl]-sesquihydrate, also known as NSC 184692, available from the NCI Developmental Therapeutics Branch. Another compound is L-aspartic acid, N-[2-chloro-5-[[(2,4-diamino-5-methyl-6-quiazolinyl)methyl]amino]benzoyl]-dihydrate, also known as NSC 132483. Another compound is L-aspartic acid, N-[2-chloro-4-[[(2,4-diamino-6-pteridinyl)methyl]amino]benzoyl]-monohydrate, also known as NSC 134033.

The loss of clonogenic survival following treatment of TSU cancer cells with NSC 184692 and 132483 has been investigated after 48 hours of exposure, and the results are listed in Table 4.

TABLE 4

Loss of Clonogenic Survival After Exposure to Methotrexate Analogs

| Concentration (μmolar) | NSC 184692 | NSC 132483 |
|---|---|---|
| 5 | 93% | 78% |
| 1 | 88% | 50% |
| 0.5 | 82% | 39% |
| 0.1 | 57% | 14% |
| 0.05 | 44% | 0% |
| 0.01 | 17% | 0% |

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a PSMA-producing cell proliferation disorder selected from prostate cancer, breast cancer, renal cancer, colon cancer, pancreatic cancer, melanoma cancer, lung cancer, and testicular cancer, the method comprising administering to a subject in need thereof a composition comprising a therapeutically effective amount of 8-0-debutanoylthapsigargin (12ADT) linked to the aspartic acid of a peptide having the sequence Asp-Glu*Glu*Glu*Glu, wherein at least one of the bonds designated with * is a gamma carboxy linkage.

2. The method of claim 1, wherein the PSMA-producing cell proliferation disorder is prostate cancer.

3. The method of claim 1, wherein the PSMA-producing cell proliferation disorder is breast cancer.

4. The method of claim 1, wherein the composition is administered parenterally by injection or by gradual infusion over time.

5. The method of claim 1, wherein the composition is administered intravenously, intraperitoneally, intramuscularly, subcutaneously, intracavity, or transdermally.

6. The method of claim 1, wherein the PSMA-producing cell proliferation disorder is renal cancer.

7. The method of claim 1, wherein the PSMA-producing cell proliferation disorder is colon cancer.

8. The method of claim 1, wherein the PSMA-producing cell proliferation disorder is pancreatic cancer.

9. The method of claim 1, wherein the PSMA-producing cell proliferation disorder is testicular cancer.

10. The method of claim 1, wherein the PSMA-producing cell proliferation disorder is lung cancer.

11. The method of claim 1, wherein the PSMA-producing cell proliferation disorder is melanoma cancer.

* * * * *

UNITED STATES PATENT AND TRADEMARK OFFICE
CERTIFICATE OF CORRECTION

PATENT NO. : 7,767,648 B2  
APPLICATION NO. : 12/323380  
DATED : August 3, 2010  
INVENTOR(S) : John Tod Isaacs and Samuel R. Denmeade Page 1 of 1

It is certified that error appears in the above-identified patent and that said Letters Patent is hereby corrected as shown below:

In the Claims

Column 20, lines 27-37: Cancel text beginning with "1. A method of treating a PSMA-producing" to and ending "gamma carboxy linkage." and replace with the following Claim 1:

1. A method of treating a PSMA-producing cell proliferation disorder selected from the group consisting of prostate cancer, breast cancer, renal cancer, colon cancer, pancreatic cancer, melanoma cancer, lung cancer, and testicular cancer, the method comprising administering to a subject in need thereof a composition comprising a therapeutically effective amount of 8-O-(12-aminododecanoyl)-8-O-debutanoyl thapsigargin (12ADT) linked to the aspartic acid of a peptide having the sequence Asp-Glu*Glu*Glu*Glu, wherein at least one of the bonds designated with * is a gamma carboxy linkage.

Signed and Sealed this  
Eighth Day of April, 2014

Michelle K. Lee  
*Deputy Director of the United States Patent and Trademark Office*